United States Patent [19]

Wasserman

[11] Patent Number: 4,611,596
[45] Date of Patent: Sep. 16, 1986

[54] SENSORY PROSTHESES

[75] Inventor: Gerald S. Wasserman, West Lafayette, Ind.

[73] Assignee: Purdue Research Foundation, West Lafayette, Ind.

[21] Appl. No.: 196,610

[22] Filed: Oct. 14, 1980

[51] Int. Cl.⁴ .............................................. A61N 1/00
[52] U.S. Cl. ................................. 128/419 R; 623/66; 181/129
[58] Field of Search ............ 3/1, 1.1; 128/1 R, 419 R; 179/1 AL, 1 SB, 1 SD, 1 SG; 181/126, 127, 129, 130, 135

[56] References Cited

U.S. PATENT DOCUMENTS 3,385,937  5/1968  Lafon ............................... 179/107 R
3,628,538  12/1971  Vincent et al. .......................... 3/1.1
3,752,939  8/1973  Bartz .................................. 181/130

Primary Examiner—William E. Kamm
Attorney, Agent, or Firm—O'Rourke & Harris

[57] ABSTRACT

A method and system for sensory prostheses are disclosed, particularly with respect to implanted auditory prostheses and implanted visual prostheses both of which function as artificial receptors. The method and system are utilized to provide prostheses that use sensory codes which simulate the natural sensory code for recognition and identification which has been found to be the integral of the temporally dispersed receptor signal. Speech recognition is improved by incorporating temporal dispersion into cochlear prostheses and visual pattern reognition is improved by manintaining current levels below those needed for detection.

5 Claims, 5 Drawing Figures

SENSORY PROSTHESES

FIELD OF THE INVENTION

This invention relates to sensory prostheses, and, more particularly, relates to implanted auditory and visual prostheses.

BACKGROUND OF THE INVENTION

Ideas concerning the possibilities of implanted sensory prostheses have existed for almost two centuries. During the recent portion of this period, auditory prostheses were developed and later improvements were suggested by a number of investigators. Most auditory work has focused on the problem of developing a cochlear implant to directly stimulate auditory nerve fibers existing from the cochlea, although during a few investigations, electrodes have been implanted on auditory cortex. Visual prostheses were also heretofore developed with later improvements being suggested by a number of investigators. In these investigations, electrodes have been implanted on the surface of the visual cortex, thereby permitting direct stimulation of the central nervous system. In addition, a number of investigators have used animal model systems to study the anatomical and physiological consequences of using chronic implants.

It has been generally accepted that the natural sensory system is quite complex and development of sensory prostheses did not therefore prove to be an easy task. Considering the fact that the auditory nerve, for example, has approximately 30,000 nerve fibers while most auditory prostheses have had only one channel and only a few have had even a dozen channels, and further considering that the optic nerve has approximately one million nerve fibers while most visual prostheses have had only a few dozen channels, the likelihood of such prostheses having any significant benefit to patients seemed initially very small. But the performance of even the earliest prosthetic devices has demonstrated that patients could derive considerable benefit from artificial prostheses. If one is totally deprived of input from a given sensory modality, any additional information obtained via that modality will represent a tremendous improvement even if the prosthetic performance level is substantially below the performance level permitted by an intact natural sensory system.

Despite this progress in prosthetic research, two important problems still existed. One problem stems from the disparate performance of visual and auditory prostheses in the area of pattern recognition, while the second problem arises from the high current levels now necessary for pattern recognition in visual prostheses.

With respect to the first problem, visual prostheses have led to very successful pattern recognition. Patients fitted with these devices have been able to "read" Braille patterns produced by direct stimulation of their visual cortex at rates that compare well with the rates with which they "read" Braille with their finger tips. Auditory prostheses have, however, not yet led to any useful ability to recognize the auditory patterns used for speech communication. With both single channel and multichannel cochlear implants, patients have not been able to recognize randomly spoken words to any reliable degree. This is not to say, however, that such patients do not extract any information from speech. When given a limited set of words from which to choose, patients do significantly better than chance at associating a given spoken word with the corresponding member of the set. This is encouraging and suggests that these devices can be improved to mediate speech perception. At least some patients wearing these devices have expressed a feeling that the information they obtained from the cochlear prosthesis is almost good enough to understand speech. Such patients have been able to recognize the difference between speech and non-speech sounds, and even distinguish one speaker from another, but they cannot understand a spoken message.

With respect to the second problem, even though visual cortex implants have led to successful pattern recognition, the current level necessary for the production of a phosphene (i.e., a perceptible spot of light evoked by the prosthesis) is fairly high. Research on animal models indicates that sustained application of currents large enough to produce phosphene detection may also tend to produce temporary and permanent changes in brain structure and function. There is, therefore, some question at the present time about the feasibility of using visual prostheses for extended periods of time without injuring the brain.

SUMMARY OF THE INVENTION

This invention is directed toward providing a solution for the problems heretofore encountered with respect to auditory and visual prostheses through a provision of sensory codes in prostheses that simulate the natural sensory code for recognition and identification which has been found to be the integral of the temporally dispersed receptor signal.

It is therefore an object of this invention to provide an improved method and system for sensory prostheses utilizing sensory codes and prostheses simulating the natural sensory code for reception and identification.

It is still another object of this invention to provide an improved method and system for sensory prostheses utilizing the integral of the temporally dispersed receptor signal.

It is still another object of this invention to provide an improved method and system for auditory prostheses.

It is yet another object of this invention to provide an improved method and system for visual prostheses wherein visual pattern recognition is retained at current levels lower than those now needed for detection.

With these and other objects in view, which will become apparent to one skilled in the art as the description proceeds, this invention resides in the novel method, construction, combination, and arrangement of parts substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

In principle a prosthesis might be designed to replace any portion of a sensory system. Thus, the earliest sensory prostheses were eyeglasses and hearing aids. Today, the emphasis is on prostheses for patients who have sensorineural deafness because their hair cells (auditory receptors) are diseased or damaged or who are blind because their rods and cones (visual receptors) are diseased or damaged.

Figure 1:
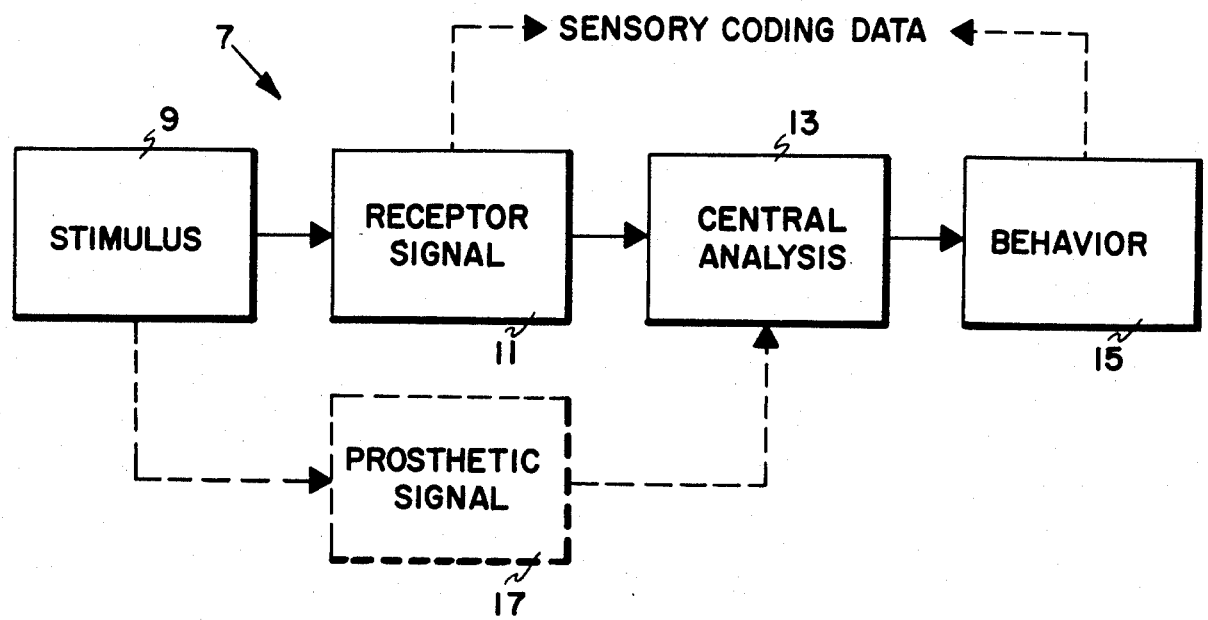
FIG. 1 is a block diagram illustrating the natural flow of sensory information and its relation to coding and prostheses as set forth in this invention.

The function of sensory receptors can be studied in two ways. One is to try to understand the way in which receptors normally encode sensory information, while the other is to try to build artifical receptors to serve as sensory prostheses for patients who are deaf or blind because disease or injury has damaged their natural receptors. FIG. 1 illustrates these two different approaches and their relation to the natural transduction and encoding of stimulus information by receptors for analysis by the central nervous system for ultimate expression in behavior.

As shown in FIG. 1, stimulus information 9 is transduced by receptors 11 into bio-electric signals which are analyzed by the central nervous system 13 and expressed in behavior 15. Two ways of studying the contributions of receptors to this process are indicated in FIG. 1. As shown, the prosthetic approach builds an artifical receptor 17 which generates an electric signal that replaces the natural receptor signal, while the sensory coding approach collects data from receptor studies and behavioral studies under comparable stimulus conditions. Sensory coding investigators then determine the features of the receptor signals (or codes) that carry information that mediates behavior by comparing data from these two different levels.

These two intimately related approaches each have something to offer the other. The design of any prosthesis will draw upon existing knowledge about natural codes and successful prostheses will, as far as possible, attempt to reproduce the most important natural codes. On the other hand, information gained from prosthetic research provides a way of testing theories of sensory coding because the human patients who are fitted with these prostheses provide information about sensation and perception that cannot ethically be obtained under any other circumstances.

Sensory coding studies indicate that the sensory code is task dependent. These studies have compared intracellular recordings from single receptors with behavior of intact human and animal subjects in order to discover the natural sensory codes that mediate sensation and perception. Problems studied have included: temporal summation; the psycho-physical function relating sensation quantity to stimulus intensity; and perceptual masking or the effect that one stimulus has on the perception of a second stimulus.

The specific conclusion that emerged is that a stimulus (light or sound) evokes a graded electrical response (receptor potential or receptor signal which is quite complex and in no way a mere copy of the stimuli. It is always possible to compare different features of the receptor response with the stimulus; in general, different features carry different information about the stimulus. Each such feature thus becomes a candidate code whose candidacy as a true sensory code is evaluated by comparing it with behavior. If a sensory code is sought that explains behavior when the subject's task is to detect a stimulus, it has been found that the feature of the receptor response (or the sensory code) that accounts for this behavior is the peak of the receptor potential. On the other hand, if accounting for behavioral competence is sought in a task where the subject is asked to recognize or to identify some aspect of the stimulus (beyond merely indicating that a stimulus is present or absent), then the sensory code is found to be the integral of the receptor potential accumulated over a period that may, in some circumstances, be several seconds.

Figure 2:
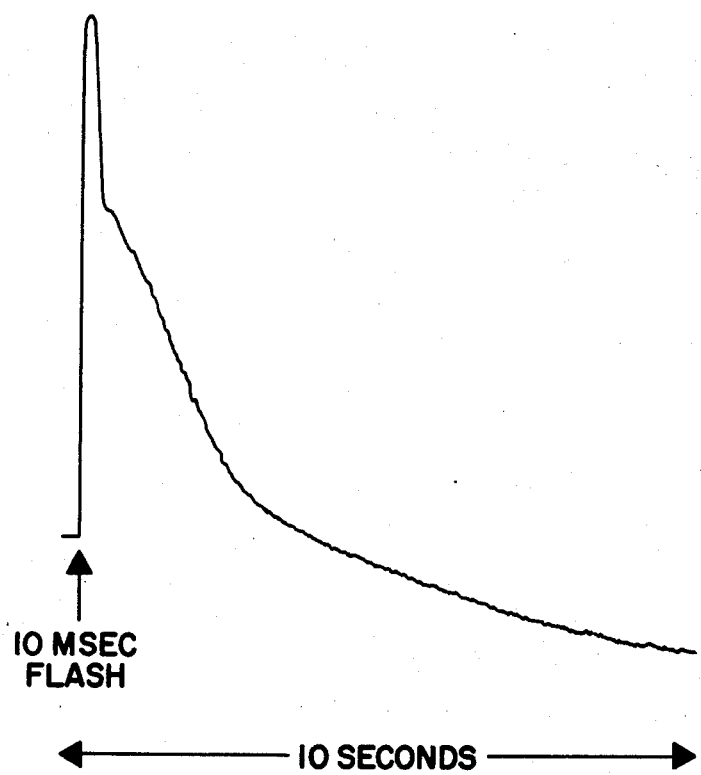
FIG. 2 is a typical response intracellular recording of a single dark-adapted photoreceptor to an intense 10 msec flash.

These two features of the receptor potential have very different properties. FIG. 2 illustrates an extreme example of this difference. A dark-adapted photoreceptor was exposed to a very intense 10 msec flash and the intracellular recording of the response is set forth in FIG. 2. As shown, this flash produced an initial rapid transient response 70 mV in amplitude. On the basis of the task dependent theory of sensory coding, the height of this initial transient is related to behavioral performance on a detection task. However, since the response is not a copy of the stimulus, the response did not disappear when the stimulus was terminated, but instead, as shown in FIG. 2, a prolonged tail developed which remained above the prestimulus baseline for some three or four seconds and then crossed below that baseline, remaining there for the rest of the 10-second interval displayed (the receptor potential did not, however, return completely to the baseline for a period of several minutes).

Contrary to expectation, this persisting tail is an essential part of the response that must be considered if one tries to account for sensation in tasks that require subjects to recognize or identify some aspect of the stimulus (in most cases, the tail or the receptor response will be considerably briefer than the tail illustrated in FIG. 2; this prolonged response was deliberately produced to emphasize the extent of persistence the receptor can exhibit). In every case examined, however, an adequate account of identification behavior hinged on whether or not the response was integrated and whether or not the persisting tail was included in the integration.

This coding evidence suggests that a necessary ingredient of any sensory prosthesis that will mediate recognition and identification is that the prosthetic signal should simulate the temporal dispersion found in the natural receptor. The coding evidence does not indicate whether temporal dispersion will be sufficient, but it does indicate that dispersion is almost certainly necessary for a successful prosthesis. Thus, it is submitted that the magnitude of the integral of the response accumulated over a prolonged period of time is the sensory code that mediates behavior in identification and recognition situations.

With respect to the foregoing, it should be noted that present auditory prostheses do not provide any temporal dispersion and have not led to successful speech recognition. While present visual prostheses generally do involve a substantial degree of temporal dispersion (even though the critical duration for phosphene detection may be less than 50 msec, cortical "Braille" has been provided by pulse trains whose pulse duration was 500 msec) and have led to successful pattern recognition. On the other hand, present auditory prostheses generally reproduce the temporal properties of the stimulus and have virtually no dispersion.

Figure 3:
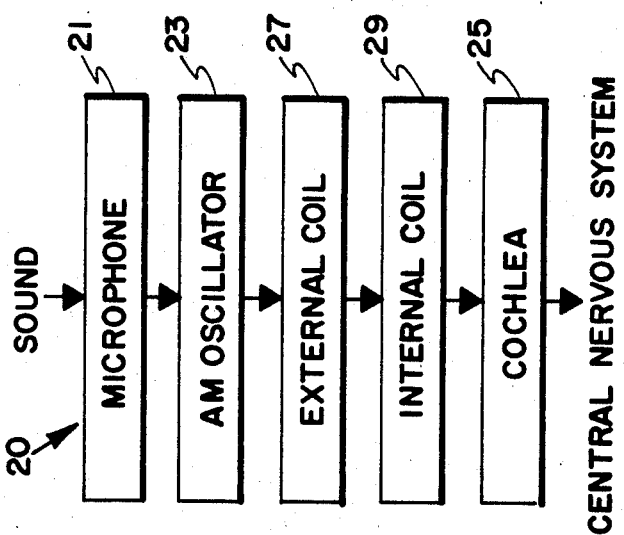
FIG. 3 is a block diagram of an electronic stimulator currently utilized in cochlear prostheses.

FIG. 3 illustrates the essential elements of an auditory prosthesis unit 20 currently known. As shown, acoustic stimuli are transduced into electrical signals with a microphone 21. Then this electrical output signal, which is a copy of the stimulus, is used to modulate an AM oscillator 23 whose carrier frequency is typically in the neighborhood of 15 kHz. This AM modulated signal is then applied to the cochlea 25 via external and internal induction coils 27 and 29, respectively, mounted on opposite sides of the skin, the internal coil 29 have a pair of wires (not shown) connected thereto, which wires are implanted inside and outside the cochlea so that the current flowing between the wires generates neural activity in the axons of the auditory nerve. Thus, the only temporal dispersion introduced by present cochlear prostheses is the dispersion attendant on the fact that the carrier frequency limits its ability to follow very rapid changes.

Introduction of temporal dispersion seemed to be counterintuitive, however, for several reasons. First any prosthesis will necessarily transmit less information than the natural sensory system. From an engineering point of view, it would therefore seem desirable to design a prosthesis so that it retained as much as possible of the limited information that prostheses may provide. By adding a circuit that spreads the auditory prosthetic signal out in time, one will obviously further degrade information that is already quite limited. Second, reports from patients already fitted with cochlear prostheses indicated that the information they obtained from their prostheses of maximum value to them was mainly temporal information. By introducing temporal dispersion into a cochlear prosthesis, this could degrade a patient's ability to utilize such temporal information. Third, dispersion would reduce the ability of the patient to obtain periodicity pitch information from the prosthetic signal.

The pattern recognition advantages of visual over auditory prostheses agrees with this conclusion reached by sensory coding studies of natural receptors; i.e., the temporal dispersion of either natural or prosthetic signals is a necessary ingredient for pattern recognition. Thus, it was found that cochlear prostheses can be substantially improved by incorporation therein of some degree of temporal dispersion.

The critical ingredient in this situation is the code that is naturally used to convey information about speech and other complex sounds to the central nervous system. The emphasis in prosthesis design should be to code the prosthetic signal so as to match the analytical requirements of the central nervous system.

Figure 4:
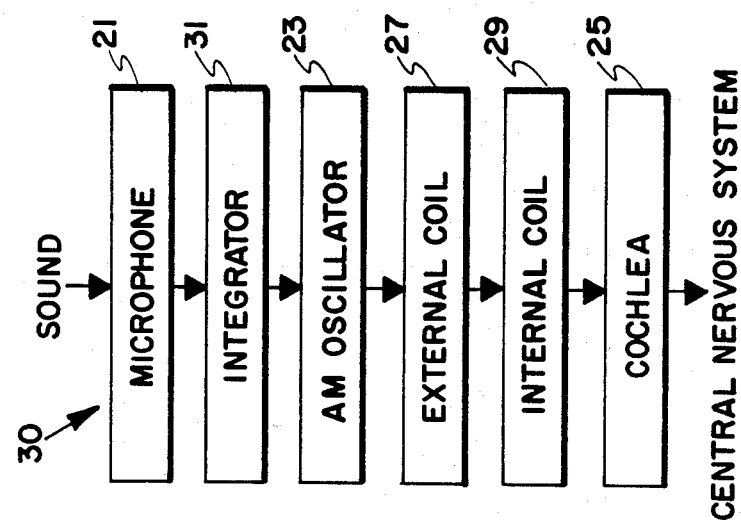
FIG. 4 is a block diagram of an electronic stimulator for cochlear prostheses having temporal dispersion through simple filtering.

As shown in FIG. 4, incorporation of temporal dispersion into existing auditory prostheses was effected in auditory prosthesis unit 30 by adding electronic integrator 31 to the circuit between microphone 21 and oscillator 23. If dispersion alone is sufficient for most speech recognition, then auditory prosthesis unit 30 can be effectively utilized. Temporal dispersion in the natural receptor, however, is known to appear only after a number of previous operations have occurred, some of which may be (and commonly are) strongly nonlinear. In this event, the dispersion introduced by the modified prosthesis unit 30, as illustrated in FIG. 4, would lead to a dispersed prosthetic signal with very different properties than the naturally dispersed receptor signal. The prosthesis unit 30 (as shown in FIG. 4) merely discards high frequency information, while natural receptors first select information from a particular portion of the auditory spectrum, then rectify and compress these signals, and finally disperse them in time.

Figure 5:
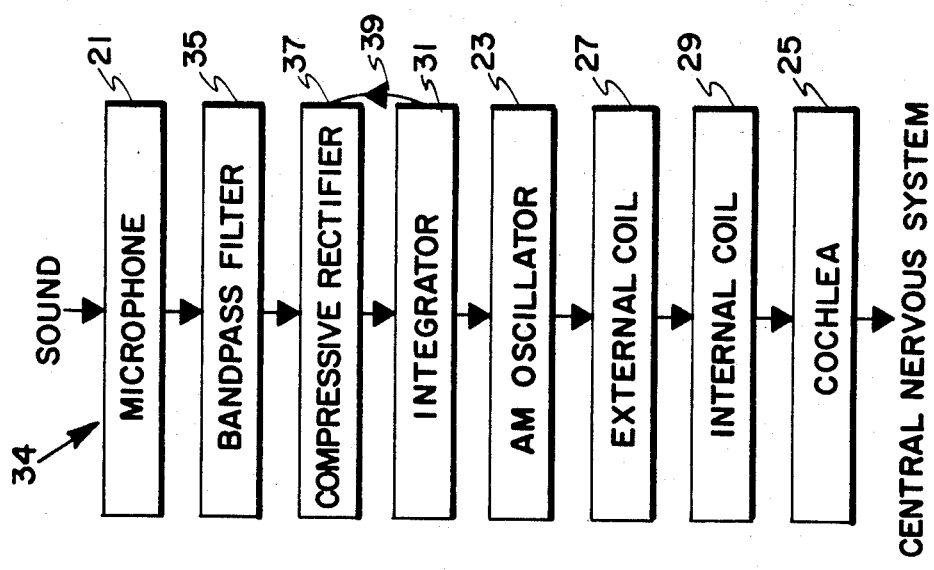
FIG. 5 is a block diagram of an electronic simulator for cochlear prostheses having a more complex type of temporal dispersion which approximates the operation of a natural receptor.

A prosthetic device 34 that stimulates the pre-dispersion operation through the natural receptor is illustrated in FIG. 5. Prosthetic system 34 is shown as a single channel device. It is not felt that a single channel cochlear prosthesis will be adequate to mediate speech perception. Experiments on normal subjects show that a great deal of speech perception remains when the auditory spectrum has been filtered to remove sounds below 1000 Hz or above 3000 Hz. Furthermore, studies done with presently known prostheses have not shown any great advantage of multi-channel cochlear prostheses over single channel designs. However, if it is shown that sufficient conditions for prosthetic speech perception should include several channels of properly dispersed signals, unit 34, as shown in FIG. 5, can be readily expanded into a multi-channel device covering a significant portion of the auditory spectrum.

As shown in FIG. 5, the essential elements of the prosthesis of this invention are:

1. A microphone 21 to transduce auditory signals into electrical signals;

2. A bandpass filter 35 to pre-emphasize speech information (with a single channel prosthesis, the bandpass filter would be fairly broadly tuned to pre-emphasize that part of the spectrum that contains the greatest amount of information about speech and to filter out extraneous sounds, while in a multi-channel device, each of the filters in each channel would be more narrowly tuned to different parts of the auditory spectrum:

3. A rectifier 37 with a nonlinear transfer function to compress the dynamic range of the prosthetic signal and to provide a DC component (a striking property of the auditory receptor potential is a nonlear relation between input intensity and output magnitude) (any sensory system, natural or prosthetic, requires a compressive nonlinearity because the dynamic range of neurons covers only two or three long units while the dynamic range of stimuli may well cover more than ten log units);

4. An electronic integrator 31 which removes most of the AC component of the prosthetic response leaving a temporally dispersed DC component (the optimal dispersion from this integrator is not currently known but it is felt that the prosthetic signal should outlast the stimulus by about five to 20 msec);

5. A feedback path 39 from the output of integrator 31 to rectifier 37 (the integrator feeds back to reduce the gain of the rectifier stage, the effect of this feedback being to emphasize the initial transient relative to the persisting tail of the response) (in coding theory terms, such feedback would favor detection at the expense of recognition. An optimal prosthesis would mediate both aspects of perception. However, since performance with any prosthesis is unlikely to be opitmal, and since speech recognition is the paramount goal, the amount of feedback should be adjusted to facilitate maximal recognition even if detection is somewhat impaired. Alternately, the amount of feedback could be under patient control to suit the momentary requirements of any particular situation); and 6. The remaining stages of the prosthesis unit 34 are (namely, AM oscillator 23, external and internal coils 27 and 29, and cochlea 25) are essentially the same as those in presently shown prosthetic stimulators such as unit 20 shown in FIG. 3 (i.e., the output of integrator 31 is coupled to AM amplitude modulator oscillator 23 whose output drives external induction coil 27, which, in turn, drives internal induction coil 29 implanted under the skin, and, which, in turn, drives electrodes implanted inside and outside of the cochlea 25).

Units 30 and 34 are improvements of presently known prosthetic simulators such as unit 20 shown in FIG. 3. The new elements are the integrator (unit 30) and the filter, rectifier and integrator (unit 34). It is to be appreciated that this invention sets forth the principles for an improved prosthesis unit, the exact parameters of which may vary for specific applications.

The same coding considerations bear on the design of visual prostheses. To date, visual prostheses have included implanting a number of electrodes on the visual cortex and then, by gradually increasing the current flowing through each electrode in turn, investigators have determined the threshhold current for producing a phosphene, which is subjectively "seen" as a spot of light that is usually localized at a particular point in the visual field. By mapping the relation of several spots to each other in the visual field, investigators have been able to choose an array of electrodes which can be simultaneously activated so as to form a visual pattern. Then the patient is asked whether or not the pattern is recognizable. As already mentioned, considerable success in recognizing patterns has been achieved. However, the problem that confronts the developers of visual prostheses at the present time is that the current strength needed for phosphene detection has often been demonstrated, as noted above, to produce long term deleterious effects when chronic implants are placed in the visual cortex of animals. A further disadvantage of high currents is that they may limit resolution because high currents also tend to influence a large area of cortex.

A solution of this serious problem appears to be available by taking account of the coding evidence that indicates that detection is mediated by a feature of the sensory signal that is quite different from the one that mediates identification. In the natural case, of course, detection almost always occurs at stimulus intensities that are below the intensities that are needed to produce identification because the intrinsic properties of receptors are such that the height of the initial transient and the length of the persisting tail of the response (as shown in FIG. 2) are related in a particular way.

The prosthesis has a great advantage in that one can create an artificial signal which independently manipulates these two aspects of the natural signal. Thus, the current strength need not be increased to the level at which phosphenes are detected (except temporarily for the purpose of mapping the implant). Instead, the current in the mapped array of electrodes is simply increased simultaneously to the level at which patterns can be recognized without being detected. This enables recognition of something that cannot be detected. Evidence already is available, however, in the literature that suggests that task dependent effects exist with prosthetic as well as natural signals (monkeys have been found to perceive a change in the prosthetic signal whose magnitude is as low as 0.02 mA, this recognition of a change occurring when a sustained signal was presented for a prolonged period of time, and this finding has been the basis of a suggestion that it might be possible to build prostheses that are effective at current levels well below phosphene detection level, it being pointed out that it takes 0.25 mA for the same monkey reliably to detect a signal and that such a current is 12.5 times greater than the change need for monkey recognition of a change.

Two possibilities emerged from the foregoing. One is to use strong currents that are above phosphene detection levels only briefly when mapping a cortical implant and then to find the sustained current level that just mediates pattern identification (the sustained current level needed for recognition will be well below the phosphene detection level if the current is maintained for a sufficiently long period of time). The second possibility is that a visual cortex prosthesis could be designed along lines that are similar to those described above with respect to the cochlear implant, namely that a visual cortex implant would recreate the important aspects of the natural receptor potential by generating a prosthetic signal with a brief initial transient followed by a small persisting signal (if cortical prosthetic signals are shaped in this fashion, obtaining of detection mediated by the initial brief signal and identification mediated by the prolonged weak signal could be effected).

In summary, sensory coding investigations of natural receptor codes have revealed that identification and recognition depend upon different aspects of the sensory signal than does detection. In particular, identification and recognition depend upon features of the receptor potential that are dispersed in time. Cochlear implants, which already have been quite successful in producing useful acoustic function, can be improved by modifying these implants so as to include a substantial degree of temporal dispersion. Implants in the visual cortex, on the other hand, which have already led to successful pattern identification but which have been hindered by the problem of damage to the cortex induced by high current strengths, can be more effectively designed by considering the critical differences between detection identification and by the difference in the sensory codes that mediate these tasks.

What is claimed is:
1. An auditory sensory prosthesis system comprising:
    transducer means for receiving acoustic stimuli and providing electrical output signals indicative thereof;
    signal processing means for receiving said output signals from said transducer means, said signal processing means including dispersion means for incorporating temporal dispersion into said signals, said dispersion means including an integrator for temporally dispersing said signals received from said transducer means, said signal processing means also including rectifier means connected between said-transducer means and said dispersion means, and said signal processing means also including feedback means connected between said integrator and said rectifier means; and
    signal applying means connected with said dispersion means for applying said temporally dispersed signal.
2. An auditory sensory prosthesis, comprising:
    a transducer for receiving acoustic signals and providing electrical signals indicative thereof;

a bandpass filter connected with said transducer to receive said electrical signals therefrom to pre-emphasize speech information;

a compressive rectifier connected with said bandpass filter to receive the filtered output signals therefrom, said rectifier compressing the dynamic range of said received signals and providing a DC component;

an electronic integrator connected with said compressive rectifier for receiving said DC component therefrom and providing a temporally dispersed DC component at the output of said integrator;

a signal feedback path from the output of said integrator to said compressive rectifier to reduce the gain of said rectifier;

an amplitude modulated oscillator connected with the output of said electronic integrator; and signal applying means connected with said oscillator for applying said oscillator output to the cochlea of a user.

3. The prosthesis system of claim 1 wherein said rectifier means has a non-linear transfer function.

4. The sensory prosthesis system of claim 2 wherein said bandpass filter pre-emphasizes that part of the spectrum that contains the greatest information about speech so as to filter out extraneous sounds.

5. The sensory prosthesis system of claim 2 wherein said electronic integrator provides a prosthesis signal that outlasts said received accoustic signal by about five to 20 msec.

* * * * *